United States Patent [19]

Freed et al.

[11] 4,251,444
[45] Feb. 17, 1981

[54] THIAZEPINO-[4,3-b]-ISOQUINOLINE-1,5-DIONE DERIVATIVES AND PRECURSORS

[75] Inventors: Meier E. Freed, Paoli; James L. Diebold, Norristown, both of Pa.

[73] Assignee: American Home Products Corporation, New York, N.Y.

[21] Appl. No.: 138,011

[22] Filed: Apr. 7, 1980

[51] Int. Cl.³ .................... C07D 513/04; A61K 31/38
[52] U.S. Cl. ................................. 260/244.4; 424/258; 546/141; 546/147
[58] Field of Search ...................................... 260/244.4

[56] References Cited
U.S. PATENT DOCUMENTS 3,383,388   5/1968   Houlihan et al. ................. 260/244.4

Primary Examiner—Donald G. Daus
Assistant Examiner—James H. Turnipseed
Attorney, Agent, or Firm—Richard K. Jackson

[57] ABSTRACT

The thiazepino-[4,3-b]-isoquinoline-1,5-diones of the formula:

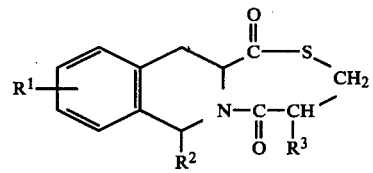

where
  $R^1$ is hydrogen, alkyl of 1 to 6 carbon atoms, alkoxy of 1 to 6 carbon atoms or halo;
  $R^2$ is hydrogen, alkyl of 1 to 6 carbon atoms or phenyl;
and
  $R^3$ is hydrogen or alkyl of 1 to 3 carbon atoms and the open ring 3-carboxy isoquinoline precursors inhibit angiotensin converting enzyme and are useful antihypertensive agents.

4 Claims, No Drawings

THIAZEPINO-[4,3-B]-ISOQUINOLINE-1,5-DIONE DERIVATIVES AND PRECURSORS

BRIEF DESCRIPTION OF THE INVENTION

The compounds of this invention, certain thiazepino-[4,3-b]-isoquinoline-1,5-diones and their 3-carboxy-isoquinoline precursors, reduce blood pressure in animals. They function as inhibitors of angiotensin converting enzyme in that they block the removal by C-terminal cleavage of the histidyl[9]-leucine[10] dipeptide from the decapeptide angiotensin I which yields the strong pressor octapeptide angiotensin II.

DETAILED DESCRIPTION OF THE INVENTION

In accordance with the invention there is provided a group of hypotensive agents of the formula:

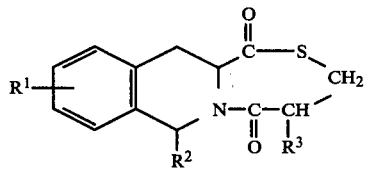

in which
$R^1$ is hydrogen, alkoxy of 1 to 6 carbon atoms, alkyl of 1 to 6 carbon atoms or halo;
$R^2$ is hydrogen, alkyl of 1 to 6 carbon atoms or phenyl;
and
$R^3$ is hydrogen or alkyl of 1 to 3 carbon atoms;
and the correspondingly substituted open ring 3-carboxy-2-(3-thiopropanoyl)-isoquinoline precursors of the structural formula:

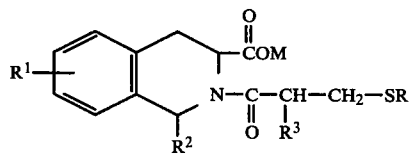

in which
R is hydrogen, alkanoyl of 2 to 6 carbon atoms or aroyl of 6 to 10 carbon atoms;
and
M is —H, or a pharmaceutically acceptable cation.

The preferred compounds of the invention, from the standpoint of economics of production, are those in which $R^1$ is hydrogen or methoxy; $R^2$ is hydrogen, methyl or phenyl; $R^3$ is hydrogen or methyl; R is hydrogen, acetyl or benzoyl and M is hydrogen or an alkali metal. When $R^1$ is halo it is intended to embrace chloro, bromo or iodo substitution.

The pharmaceutically acceptable cations representing M are those derived from bases which yield a pharmaceutically acceptable salt of the open ring 3-carboxy-2-(3-thiopropanoyl) isoquinolines. The salts may be derived from either inorganic or organic bases to yield ammonium salts; alkali metal salts (sodium, potassium, etc.); alkaline earth salts, preferably calcium or magnesium; lower alkylamine salts; di(lower)alkylamine salts; tri(lower)alkylamine salts and the corresponding omega-hydroxy analogues (e.g. methylamine, ethylamine, propylamine, dimethylamine, diethylamine, dipropylamine, trimethylamine, triethylamine, tripropylamine, di(hydroxyethyl)amine, and the like). Similarly more complex amines which are employed in depot administration for slow release into the body, such as $N,N^1$-dibenzylethylenediamine, are applicable bases for pharmaceutically acceptable salt formulation.

The compounds of this invention are produced by acylation of an appropriately substituted 1,2,3,4-tetrahydroisoquinoline-3-carboxylic acid of the formula:

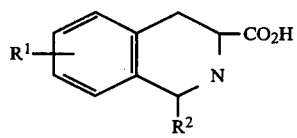

where $R^1$ and $R^2$ are defined above in aqueous alkaline solution with a substituted propionyl halide of the formula:

where
X is chloride or bromide;
$R^3$ is hydrogen or alkyl of 1 to 3 carbon atoms; and
Y is chloro, bromo, alkanoylthio of 2 to 6 carbon atoms or aroylthio of 6 to 10 carbon atoms.

Where Y is chloro or bromo, the intermediate product is reacted with a thioalkanoic acid or thioaromatic carboxylic acid alkali metal salt to introduce the mercapto function at 3-position of the propanoyl moiety. The 3-acylthiopropanoyl substituted products are converted to the free mercaptopropanoyl derivatives by treatment with a base followed by acidification. The 2-(3-mercaptopropanoyl)-1,2,3,4-tetrahydroisoquinoline-3-carboxylic acid derivatives are ring closed to afford the 1,4-thiazepine ring by conventional activation of the carboxyl group, e.g. as an activated ester, mixed anhydride, carbodiimide, acyl halide, etc. The use of $N,N^1$-dicyclohexylcarbodiimide (DCC) is a preferred activating reagent because of the facility of the ring closure and ease of removal of the dicyclohexyl urea byproduct.

The pharmaceutically acceptable salts of the 3-carboxy isoquinoline compounds are produced in a conventional manner by neutralization of the acid with an equivalent of the desired base.

The starting compounds for production of the compounds disclosed herein are either known or readily preparable by the chemist employing known techniques.

The thiazepino-[4,3-b]-isoquinoline-1,5-diones and their 3-carboxy-isoquinoline precursors, depicted above, inhibit the conversion of angiotensin I to angiotensin II, thereby alleviating hypertension caused by the strong pressor action of the latter octapeptide. The compounds are administered to the hypertensive animal in single or divided doses, orally or parenterally, at a dose from about 0.1 to 150 milligrams per kilogram per day. The preferable dosing regimen provides from about 1 to 50 milligrams per kilogram per day, depending upon the severity of the hypertensive state. Oral administration in solid form by tablet or capsule may be accomplished with the compounds of this invention in neat or pure form, alone or in combination with conventional adjuvants. Similarly, parenteral administration may be accomplished with physiological saline or via suspension in conventional vehicles. In any event, the dosing regimen must be individualized by the attending physician for the patient based upon the severity of the dysfunction.

The activity of the compounds of this invention was established by incubation of the hippuryl-L-histidy-L-leucine at 37° C. with angiotensin converting enzyme by the following procedure:

A crude angiotensin converting enzyme supernatant is obtained by blending 1 gm. of rabbit lung acetone powder (Pel-Freez Biologicals) with 35 ml of 50 mM (buffered) potassium phosphate, pH 8.3 and centrifuging for 45 min. at 40,000 xg.

The specific angiotensin converting enzyme substrate Hippuryl-L-histidyl-L-leucine (HHL—Sigma Chem. Co.) is prepared at 5 mM in 200 mM potassium phosphate buffer containing 757 mM NaCl at pH 8.3.

Incubation for the assay of HHL hydrolysis by angiotensin converting enzyme is carried out in a 37° C, gyrorotary incubator in disposable 13×100 mm tubes. Each 0.25 ml asay mixture contains the following components at the final concentrations: potassium phosphate buffer, 100 mM; NaCl, 300 mM, 5 mM; and enzyme 0.15 ml (10 mU approx.) added last to initiate the reaction. Zero time controls have 0.25 ml of 2 N HCl added before the enzyme. The timed reactions are terminated with acid at 30 min. similarly and the hippuric acid freed from the substrate is extracted into 1.5 ml of ethylacetate by vortex mixing for 15 sec. After 5 min. centrifugation in a clinical centrifuge, a 1.0 ml aliquot of the ethyl acetate layer is transferred to a clean tube. These aliquots are evaporated to dryness by heating (120° C.) in a Temp-Block module heater.

The hippuric acid is resuspended in 1.0 ml of water, the absorbance at 228 nm is determined, and the amount present is calculated from a standard curve. The amount of hippuric acid x 1.1 (extraction coefficient)×1.5 (ratio of volumes)×1 $\mu$M hippuric acid/200 $\mu$g×1/30 min=nM hippuric acid released/min. Enzyme activity in the presence of an inhibitor is compared with control activity, and reported as a percentage inhibition. (Cushman, D. W. and Cheung, H. S., Biochem. Pharmacol. 20 1637 (1971).

The in vitro experiments were confirmed following the procedure of Rubin et al, J. Pharmacol. Exp. Ther 204 721 (1978) following the procedure whereby jugular vein and carotid artery cannulae are placed in an ether anesthetized, normotensive, male, Sprague-Dawley rat for injection of compounds and direct recording of systemic arterial pressure, respectively. The blood pressure responses to i.v. injections of angiotensin I (300 ng/kg), angiotensin II (100 ng/kg) and bradykinin (10 $\mu$g/kg) are recorded and compared with identical doses administered at various time intervals after oral dosing of the angiotensin converting enzyme inhibitor of this invention.

In addition, the blood pressure lowering ability of the compounds of this invention was established by measuring the systolic pressure of male spontaneously hypertensive rats with a Decker Caudal Plethysmograph. The compounds tested were administered orally and blood pressure was read prior to and at 1.5, 4 and 24 hours after drug administration.

As representative compounds of the invention, 100 nanograms of the product of example two, infra, inhibited angiotensin converting enzyme by 40 percent in the above described in vitro test and demonstrated moderate inhibition in vivo at 10 milligrams dose. Similarly, 100 nanograms of the product of example four inhibited angiotensin converting enzyme by 70 percent and reduced the blood pressure of the standard experimental rat by 29 millimeters at four hours after administration of a 50 milligram dose.

The following examples illustrate the preparation of representative compounds of this invention.

EXAMPLE 1

2-(3-Acetylthiopropanoyl)-1,2,3,4-Tetrahydroisoquinoline-3-Carboxylic Acid

To a solution of 1,2,3,4-tetrahydroisoquinoline-3-carboxylic acid (5.0 g., 0.028 M) and sodium hydroxide (2.26 g., 0.056 M) in water (100 ml.) at 10° C. is slowly added 3-bromopropionyl chloride (2.84 ml., 0.028 M). This mixture is stirred at 25° C. overnight. Potassium thiolacetate, prepared by mixing thiolacetic acid (3.00 ml., 0.042 M) and potassium carbonate (3.90 g., 0.028 M) in water (30 ml.), is added to the reaction mixture which is stirred at 25° C. overnight to yield the title compound as an alkali metal salt. Acidification with dilute hydrochloric acid affords the free carboxylic acid.

EXAMPLE 2

2-(3-Mercaptopropanoyl)-1,2,3,4-Tetrahydroisoquinoline-3-Carboxylic Acid

Ammonium hydroxide (5 ml.) is added to the reaction mixture of the preceding example and stirred at 25° C. for 2 hours. The precipitate which is obtained upon acidification with dilute hydrochloric acid, is extracted into methylene chloride. The extract is washed, dried over sodium sulfate and evaporated to give a tan solid, the title compound, m.p. 55°–58° C.

Anal. Calcd. for: $C_{13}H_{15}NO_3S.1/6CH_2Cl_2$:
Calculated: C, 56.58; H, 5.53; N, 5.01;
Found: C, 56.70; H, 5.22; N, 4.99.

EXAMPLE 3

3,4,12,12a-Tetrahydro-5H[1,4]Thiazepino[4,3-b]-Isoquinoline-1,5(7H)-dione

The compound produced in Example 2 is dissolved in about 500 milliliters methylene chloride and the solution is chilled under nitrogen to 15° C. in a dry ice-acetone mixture. 4-Dimethylaminopyridine is added and the mixture is stirred for five minutes. A slight excess of dicyclohexylcarbodiimide dissolved in methylene chloride is added with stirring. The chilling source is removed after 15 minutes and the solution is stirred overnight at room temperature. The volume of the reaction mixture is reduced on a rotary evaporator under reduced pressure to about 100 milliliters. A precipitate is removed by filtration and the filter residue is washed several times with methylene chloride. The filtrate and combined washings are washed successively with 1 N, HCl, saturated aqueous $NaHCO_3$, water and saline and the solution is dried over $MgSO_4$. Evaporation of the methylene chloride with a rotary evaporator under reduced pressure yields a white solid which is recrystallized from diethyl ether to yield the title compound.

EXAMPLE 4

2-(3-Benzoylthio-2-methylpropanoyl)-1,2,3,4-tetrahydroisoquinoline-3-carboxylic acid To a solution of (−)1,2,3,4-tetrahydroisoquinoline-3-carboxylic acid (5.0 g., 0.028 M) and sodium hydroxide (1.12 g., 0.028 M) in water (100 ml.) at 10° C. was slowly added (−)3-benzoylthio-2-methylpropionyl chloride (6.82 g., 0.028 M). At the same time, from a separate dropping funnel, was added a solution of sodium hydroxide (1.12 g., 0.028 M) in water (20 ml.), at such a rate that the solution was maintained at a pH between 9.5 and 7.5 pH units (final pH 7.5). After stirring overnight at 5° C., the reaction mixture was filtered and the clear filtrate acidified with dilute hydrochloric acid. The product was extracted into methylene dichloride, washed and dried over sodium sulfate. After filtration the solvent was removed by evaporation at reduced pressure, leaving a residue (8 g.). To a solution containing 0.5 g of this material in methylene dichloride was added piperazine (0.058 g., 0.67 mM). The solvent was removed and the product recrystallized from acetonitrile, giving a white solid, the title compound, as a hemipiperazine salt, m.p. 154°–155° C.

Analysis for: $C_{23}H_{26}N_3SO_4 \cdot 0.5\ H_2O$:
Calculated: C, 63.42; H, 6.25; N, 6.43;
Found: C, 63.96; H, 6.12; N, 6.51.

EXAMPLE 5

2-(3-Mercapto-2-methyl-propanoyl)-1,2,3,4-tetrahydroisoquinoline-3-carboxylic acid Following the procedure of Example 2, the benzoyl group is removed from the product of Example 4 by ammonolysis and subsequent acidification to yield the title compound.

EXAMPLE 6

3,4,12,12a-Tetrahydro-5H-[1,4]thiazepino[4,3-b]-isoquinoline-1,5(7H)-dione

Following the procedure of Example 3, the product of Example 5 is cyclized with dicyclohexylcarbodiimide to afford the title compound.

EXAMPLE 7

2-(3-Benzoylthio-2-methylpropanoyl)-1,2,3,4-tetrahydroisoquinoline-3-carboxylic acid To a solution of (−)-1,2,3,4-tetrahydroisoquinoline-3-carboxylic acid (7.0 g., 0.04 M) and sodium hydroxide (1.6 g., 0.04 M) in water (160 ml.) at 10° C. was slowly added (−)-3-benzoylthio-2-methylpropionyl chloride (9.7 g., 0.04 M). At the same time, from a separate dropping funnel, was added a solution of sodium hydroxide (1.6 g., 0.04 M) in water (15 ml), at such a rate that the solution was maintained at a pH between 9.5 and 7.5 pH units (final pH 7.5). After stirring overnight at 5° C., the reaction mixture was filtered and the clear filtrate acidified with dilute hydrochloric acid. The product was extracted into methylene chichloride, washed and dried over sodium sulfate. After filtration the solvent was removed by evaporation at reduced pressure, leaving a residue (14 g.). This material was separated on an HPLC preparative column (Prep Pak $C_{18}$ column, Waters) using a mobile phase of 50 parts methanol, 50 parts water and 0.5 parts acetic acid. Two main fractions were obtained, 15% and 84%. The residue from the major fraction was dissolved in ether, washed and dried over sodium sulfate. After filtration the solvent was removed by evaporation at reduced pressure, leaving a white solid, the title compound (10 g.), m.p. 61–63, $[\alpha]_D^{25} = -76.39$ (C = 1.55% EtOH.

Anal. Calcd. for: $C_{21}H_{21}NSO_4$:
Calculated: C, 65.77; H, 5.52; N, 3.65;
Found: C, 65.21; H, 5.68; N, 3.42

What is claimed is:

1. A compound of the formula:

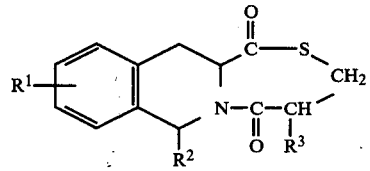

in which $R^1$ is hydrogen, alkoxy of 1 to 6 carbon atoms, alkyl of 1 to 6 carbon atoms or halo;

$R^2$ is hydrogen, alkyl of 1 to 6 carbon atoms or phenyl;

and $R^3$ is hydrogen or alkyl of 1 to 3 carbon atoms.

2. A compound of claim 1 of the formula:

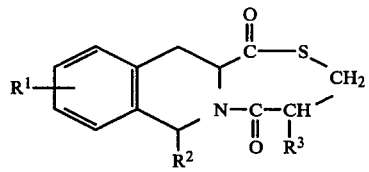

in which $R^1$ is hydrogen or methoxy;

$R^2$ is hydrogen, methyl or phenyl;

and $R^3$ is hydrogen or methyl.

3. The compound of claim 2 which is 3,4,12,12a-tetrahydro-5H-[1,4]thiazepino-[4,3-b]-isoquinoline-1,5(7H)-dione.

4. The compound of claim 2 which is 3,4,12,12a-tetrahydro-4-methyl-5H-[1,4]thiazepino[4,3-b]-isoquinoline-1,5(7H)-dione.

* * * * *

Notice of Adverse Decision in Interference

In Interference No. 100,949, involving Patent No. 4,251,444, M. E. Freed and J. L. Diebold, THIAZEPINO-(4,3-B)-ISOQUINOLINE-1,5-DIONE DERIVATIVES AND PRECURSORS, final judgment adverse to the patentees was rendered Apr. 22, 1986, as to claims 1–3.

[*Official Gazette October 7, 1986.*]